United States Patent [19]

Nakajima et al.

[11] 4,359,308

[45] Nov. 16, 1982

[54] COUNTERBALANCE DEVICE FOR LASER KNIFE

[75] Inventors: Tohru Nakajima, Tokyo; Koichi Kamoi, Yoshikawa, both of Japan

[73] Assignee: Asahi Kogaku Kogyo Kabushiki Kaisha, Tokyo, Japan

[21] Appl. No.: 110,168

[22] Filed: Jan. 7, 1980

[30] Foreign Application Priority Data

Jan. 29, 1979 [JP] Japan ................................ 54-9017

[51] Int. Cl.³ ............................................. A61B 17/36
[52] U.S. Cl. .................................... 414/719; 414/917; 414/1; 248/280.1; 128/303.1
[58] Field of Search ........................... 414/1, 719, 917; 128/303.1, 395; 248/648, 280–281, 281.1, 123.1, 325

[56] References Cited

U.S. PATENT DOCUMENTS

| 3,489,384 | 1/1970 | Perbal | 248/280.1 |
| 3,528,424 | 9/1970 | Ayres | 128/303.1 |
| 3,913,582 | 10/1975 | Sharon | 128/303.1 |
| 3,994,464 | 11/1976 | Perbal | 248/280.1 |
| 4,241,891 | 12/1980 | Rudolph | 248/123.1 |

Primary Examiner—Robert J. Spar
Assistant Examiner—Terrance L. Siemens
Attorney, Agent, or Firm—Sughrue, Mion, Zinn, Macpeak & Seas

[57] ABSTRACT

A counterbalance device for operation with the manipulator of a laser knife in which the moment of the knife is maintained in a balanced state over the entire range of movement of the knife so that the movement of the knife is smooth over its entire range and its operability highly increased. A counterbalance device of the invention is coupled to the manipulator at a fulcrum point. The centers of gravity of the manipulator and counterbalance device are in the same vertical plane. The center of gravity of the counterbalance device is moved in parallel with the movement of the center of gravity of the manipulator. In preferred embodiments, the counterbalance device includes arm sections which are geometrically similar to the arm structure of the manipulator device. A rotatable arm of the counterbalance device is coupled through rotatable links to the corresponding rotatable arm of the manipulator so as to maintain dynamical balance.

5 Claims, 6 Drawing Figures

COUNTERBALANCE DEVICE FOR LASER KNIFE

BACKGROUND OF THE INVENTION

This invention relates to a counterbalance device for a manipulator of, for instance, a laser knife in which the moment of the knife within the permissible range of movement thereof is maintained in a balanced state so that the operability of the device is remarkably improved.

The manipulator of a laser knife is a device in which several hollow light conducting paths of different lengths are coupled to one another by means of mirrors to form a single flexible light conducting path for introducing and focusing laser beams emitted by a laser oscillator onto a desired position.

Typically, the weight of such a manipulator is several kilograms. The dynamical fulcrum which is provided for supporting the manipulator is positioned in the vicinity of the input end of the laser beams. The position of the center of gravity of the manipulator is irregularly shifted as the manipulator is operated and, accordingly, the moment of the manipulator with respect to the dynamical fulcrum is also irregularly changed. To compensate for this, a counterbalance device may be provided the prime purpose of which is to provide selected weight on the side opposite, with respect to the dynamical fulcrum, to the manipulator to support the latter and to thereby eliminate moment unbalance due to movement of the center of gravity of the manipulator.

A conventional counterbalance device for a laser knife is so designed that, as described in the specification of U.S. Pat. No. 3,913,582, the moment is maintained in a balanced state only when the manipulator rests at a single predetermined position. Such a conventional counterbalance device is disadvantageous in the following points. First, it cannot eliminate moment unbalance due to movement of the center of gravity of the manipulator. Secondly, the moment is increased or decreased in proportion to the amount of shift of the center of gravity of the manipulator from its initial position. This unbalance of moment produces a high resistance to manual movement by the operator when he is operating the manipulator. This is a serious disadvantage in a surgical operation as it may distract the operator from concentrating his attention on the delicate techniques usually involved in such procedures.

Accordingly, a first object of the invention is to eliminate moment unbalance caused by movement of the center of gravity of a manipulator as the latter is operated by continuously controlling a counterbalance system in association with the operation of the manipulator.

A second object of the invention is to improve the operability of the manipulator for both fine and coarse operational modes by eliminating moment unbalanced states.

A third object of the invention is to maintain the moment balance of the manipulator stable at all times thereby to protect its multi-articulation mirror coupling mechanism from excessive force and to maintain the required extremely high stability of the laser beam light conducting system and its optical axis.

SUMMARY OF THE INVENTION

In accordance with these objects of the invention, there may be provided a counterbalance device for laser knife having a manipulator and means for counterbalancing the manipulator. The counterbalance means is coupled to the manipulator at a fulcrum point. The counterbalance means is so arranged that in an initial position thereof moment balance with respect to the manipulator and counterbalance is maintained at the fulcrum point and the centers of gravity of the manipulator and the counterbalance lie in the same vertical plane. Also, during the operation of the device, a plane along which the center of gravity of the manipulator moves is parallel to a plane along which the center of gravity of the counterbalance moves. In this fashion, moment balance attributed to movement of the center of gravity of the manipulator is maintained for all positions within the range of movement of the device.

In one embodiment, the counterbalance means includes a counterbalance arm section geometrically similar to a corresponding manipulator arm section. The counterbalance arm section is fixedly connected to one end of an arm of the manipulator arm section. The weight of the counterbalance arm section is determined so that the counterbalance arm section is in moment balance with the manipulator arm section with one end of the arm of the manipulator section acting as the fulcrum. A rotatable manipulator arm is linked to a coupling point so as to be rotatable around an end arm of the counterbalance arm section. The length and weight of the rotatable arm are determined so as to maintain moment balance with a corresponding rotatable arm of the manipulator with respect to the fulcrum. There is further provided a rod and rotatable links for coupling ends of the rod respectively to the rotatable arms of the manipulator and counterbalance means so as to form a quadrilateral parallelogram at all positions of the manipulator with the corners of the parallelogram being formed by the ends of the rod and junctures of the rotatable arms with the end arms. Moment balance attributed to movement of the center of gravity of the manipulator is thereby maintained.

In another embodiment, the device includes an arm fixedly connected to one end of an arm of the manipulator arm section at the fulcrum. The length and weight of the arm are selected so that the arm is in moment balance with the manipulator arm section at the fulcrum. A first arm of the counterbalance means is fixedly coupled to one end of the arm of the manipulator arm section extending parallel to a corresponding arm of the manipulator arm section. A second arm of the counterbalance means is linked so as to be rotatable around a connection point in a plane in which lies the first arm and a rotatable arm of the manipulator. The length and weight of the second arm are selected so as to place the arm in moment balance with the rotatable arm of the manipulator with respect to the fulcrum. There is further provided a rod and rotatable links rotatably coupling ends of the rod respectively to the rotatable arms of the manipulator and counterbalance means.

In yet a further embodiment, the device includes a counterbalance arm section fixedly connected to one end of a first manipulator arm at the fulcrum. The counterbalance arm section has a 90° bend at a connection point on a first arm of the counterbalance arm section forming an extension of the first manipulator arm at which bend is joined a first end of a second arm of the counterbalance arm section which is disposed parallel to a second arm of the manipulator joined to the first arm of the manipulator. A rotatable arm is provided to the counterbalance means which is linked so as to be rotatable around a second end of the second arm of the counterbalance arm section in parallel with a plane formed by a rotatable arm of the manipulator joined to an end of a third arm of the manipulator the other end of which is joined to the second arm of the manipulator and a line between the fulcrum and the juncture between the rotatable arm of the manipulator and the third arm thereof. The length and weight of the rotatable arm of the counterbalance section are selected so as to maintain moment balance with the manipulator with respect to the fulcrum. An arm is further fixedly connected to the third arm of the manipulator and a rod and rotatable links are provided with the rotatable links coupling ends of the rod respectively to the arm fixedly connected to the third arm of the manipulator and the rotatable arm of the counterbalance means. A quadrilateral parallelogram is formed by the ends of the rod, the juncture point of the third arm of the manipulator and the arm connected thereto, and the fulcrum, the parallelogram being maintained for all positions of the manipulator.

DESCRIPTION OF THE PREFERRED EMBODIMENTS

A counterbalance device for a laser knife according to this invention will be described in detail with reference to its preferred embodiments shown in the accompanying drawings.

Figure 1:
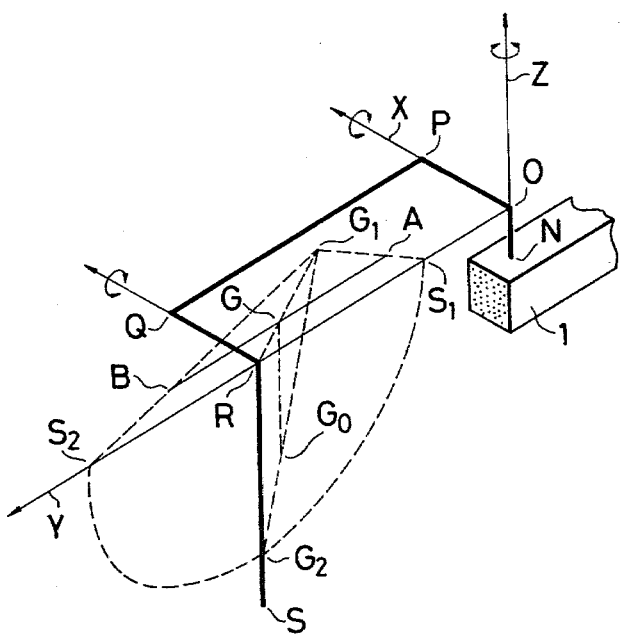
FIG. 1 is a perspective view of a dynamical arrangement of a manipulator device.

FIG. 1 shows the dynamical arrangement of the manipulator of a laser knife device. A laser beam emitted by an oscillator 1 is introduced through an internal reflecting mirror to an exit point N and is then applied through an arm NO to a fulcrum (origin point) O. After this, the laser beam passes through arms, OP, PQ, QR and RS in that order and reaching a manipulator head provided at the end S of the arm RS. A mirror device is incorporated in each of the connections O, P, Q, R and S of the arms to turn the laser beam through 90°. The manipulator head can be moved to a desired position in the field of operation by a suitable combination of rotational motions of the three arms NO, OP and QR.

A variety of methods for introducing a laser beam to a desired position in the field of operation by means of a multi-articulation mirror coupling mechanism have been proposed. A typical one of these conventional methods is as shown in FIG. 1 described above. The manipulator is connected to the laser oscillator at one end N of the arm NO. The dynamic system thereof is constituted by a symmetrical revolution system around the arm NO, that is the Z-axis. Therefore, analysis of the dynamical system can properly be made with respect to an X-Y plane with the manipulator arm OP as the X-axis and with a line connecting the points O and R as the Y-axis.

FIG. 1 shows a state of the manipulator in which the arm section OPQR lying in the X-Y plane is perpendicular to the Z-axis and the arm RS extends downwardly parallel to the Z-axis. This position is hereinafter referred to as "the initial position" when applicable. The center of gravity $G_0$ of the manipulator lies at an internal dividing point of a segment connecting the center of gravity $G_1$ of the arm section OPQR and the center of gravity $G_2$ of the arm RS. However, the position of the center of gravity $G_0$ is, in general, varied by the operation of the manipulator in a complex manner. The projection G of the center of gravity $G_0$ onto the X-Y plane is displaced along a segment AB in parallel with the Y-axis because the center of gravity $G_2$ moves along an arc $S_1G_2S_2$ with point R as its center. This is an effect of the revolution of the arm QR and it does not depend at all on the revolution positions of the arms NO and OP.

Figure 2:
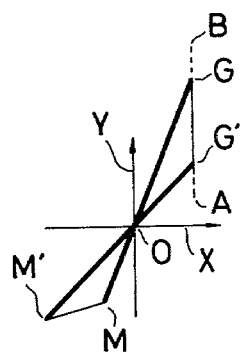
FIG. 2 is a diagram used for a description of the dynamical principles of a counterbalance device.

FIG. 2 is a projection of the system of FIG. 1 onto the X-Y plane which is useful for a description of the dynamical principles of the counterbalance device. The purpose of use of the counterbalance device is to eliminate unbalance of moment attributed to the movement of the center of gravity of the manipulator. First, in the initial position, the center of gravity of the counterbalance is placed at a point M on a straight line connecting the projection of the center of gravity onto the X-Y plane and the fulcrum O so as to provide a weight $W_M$ which is determined from a balancing condition equation $W_M \cdot \overline{OM} = W \cdot \overline{OG}$, where W is the total weight of the manipulator.

As was described before, the projection G moves along the segment AB parallel to the Y-axis. Therefore, when the center of gravity of the manipulator moves from its initial position to a position G', it is necessary that the center of gravity of the counterbalance move to a point M' on a straight line which connects the projection G' and the fulcrum O and that a weight $W'_M$, which is defined by a balancing conditional equation $W'_M \cdot \overline{OM} = W \cdot \overline{OG'}$, be applied.

In FIG. 2, reference characters GOM and G'OM' designate the dynamical systems in a first balance state in the initial position and in a second balance state after the movement of the center of gravity, respectively. The center of gravity of the manipulator is continuously moved along the segment AB. Therefore, in order to maintain a balanced moment at all times, it is necessary to continuously maintain a balanced condition in the course of shifting from the dynamical system GOM to the dynamical system G'OM'. However, continuously maintaining the balanced condition by simultaneously varying the weight of the counterbalance and the lengths of the arms thereof is theoretically possible but is not practical.

Figure 3:
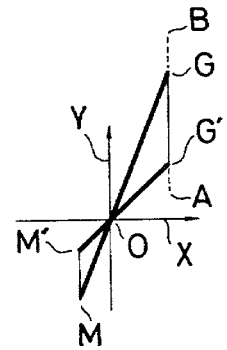
FIG. 3 is a diagram showing the projection of the gravity center systems of a counterbalance and a manipulator onto an X-Y plane.

FIG. 3 shows the dynamical principle of a counterbalance device according to the invention in which, with the weight $W_M$ of the counterbalance maintained unchanged, the moment balancing condition of the manipulator is continuously maintained irrespective of the movement of the center of gravity of the manipulator to thus eliminate the unbalance of the moment attributed to the movement of the center of gravity at all times.

FIG. 3 is a projection of the system of FIG. 1 onto the X-Y plane similar to the case of FIG. 2. The segment AB in parallel with the Y-axis is the range of movement of the projection G of the center of gravity of the manipulator onto the X-Y plane. The specific features of the counterbalance device according to the invention are as follows.

The segment GG' along which the center of gravity of the manipulator is moved is parallel to the segment MM' along which the center of gravity of the counterbalance is moved. The points G, O and M are on one straight line while the points G', O and M' are on another straight line. In addition the triangle GOG' is maintained geometrically similar to triangle MOM' with respect to the fulcrum O. The weight $W_M$ of the counterbalance is obtained by multiplying the weight W of the manipulator by the reciprocal of the ratio of similitude of the aforementioned triangles.

Figure 4:
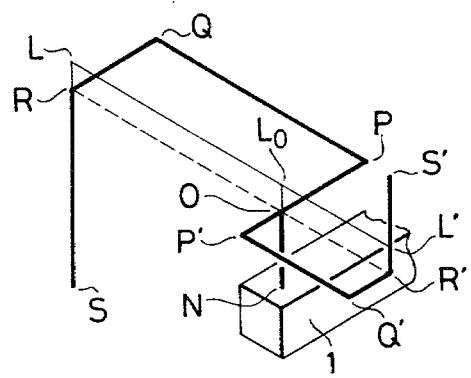
FIG. 4 is a perspective view of the dynamical arrangement of an example of a counterbalance device according to the invention.

FIG. 4 illustrates the dynamical arrangement of one example of the counterbalance device according to the invention. The counterbalance device includes a counterbalance arm section OP'Q'R' geometrically similar to a manipulator arm section OPQR and fixedly coupled to one end O of the arm OP. The section OP'Q'R' being applied with a weight which maintains it in moment balance with the section OPQR with the point O as the fulcrum. Also included is an arm R'S' which is linked to the connection R' of the arm Q'R' so as to be rotatable around the arm Q'R' the length and the weight of the arm R'S' being so determined as to be in moment balance with the arm RS with respect to the fulcrum O.

Rotatable links L and L' are provided on the arms RS and R'S' or on the extensions thereof, respectively. Furthermore, the counterbalance device is provided with a rod LL' which is coupled through a slidable support point Lo which is on the extension of the arm NO. The rod LL' forms a rectangle RLL'R' with the points R and R'. The rectangle RLL'R' is maintained as a parallelogram so that the movement of the arm RS due to the operation of the manipulator is coupled directly to the movement of the arm R'S' so that a balanced moment condition of the two arms with respect to the fulcrum O is maintained at all times.

Thus, the manipulator arm section OPQR is fixedly coupled through the fulcrum to the counterbalance arm section OP'Q'R' which is geometrically similar thereto. These two sections are turned as a single unit around the arms NO and PP'. The manipulator arm RS and the counterbalance arm R'S' are rotatably coupled to each other through the rod LL' forming the parallelogram RLL'R'. Therefore, the manipulator and the counterbalance entirely eliminate unbalance in the moment of the system to the movement of the center of gravity of the manipulator. This completely satisfies the moment balancing condition described in conjunction with FIG. 3.

In the rod LL' coupling the arm RS to the arm R'S', the lengths of the arms RS and R'S' may be selected as desired as long as they form the parallelogram RLL'R'. The rod LL' may be positioned above the fulcrum O as shown in FIG. 4 or may be positioned below the fulcrum O. The rod LL' is provided to transmit the rotation of the arm RS to the arm R'S' to rotate the latter while maintaining a balanced condition. Accordingly, it is not always necessary to provide the link L on the arm RS or on the extension of the latter as in the example shown in FIG. 4. That is, an arm TL as shown in FIG. 6 and which will be described below may be fixedly coupled, similarly to the part RL, to the arm QR which is the rotary axis of the manipulator or to the extension of the arm QR in such a manner that the points R, L, L' and R' form a parallelogram at all times.

Figure 5:
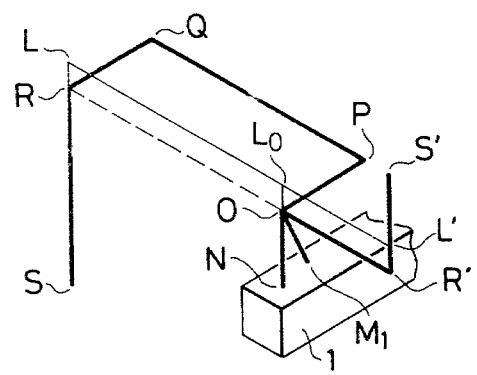
FIG. 5 is a perspective view of the dynamical arrangement of another example of the counterbalance device according to the invention.

FIG. 5 illustrates the dynamical arrangement of another example of the counterbalance device according to the invention. This version of the counterbalance device includes an arm $OM_1$ fixedly connected to one end O of a manipulator arm OP, the length and the weight of the arm $OM_1$ being determined so that it is in moment balance with a manipulator arm section OPQR with the point O as the fulcrum. Also included is an arm section OR'S' having an arm OR' which is connected to one end O of the arm OP and is in parallel with the arm PQ and an arm R'S' which is linked rotatably around a connection R' in a plane SROR' with the length and the weight of the arm R'S' being determined such that it is in moment balance with the arm RS with respect to the fulcrum O. The device further includes rotatable links L and L' provided respectively on the arms RS and R'S' or on the extensions thereof and a rod LL' which is provided completely analogous to the example described with reference to FIG. 4.

Thus, the manipulator arm section OPQR and the counterbalance arm $OM_1$ are fixedly connected to each other so that they are in moment balance with each other with respect to the fulcrum O while the manipulator arm RS and the counterbalance arm R'S' are rotatably coupled to each other through the rod LL' forming the parallelogram RLL'R'. Therefore, the manipulator and the counterbalance together operate to eliminate entirely any moment unbalance attributed to the movement of the manipulator. This fully satisfies the moment balancing conditions described with reference to FIG. 3. Similar to the example shown in FIG. 4, the position of the link L may be changed in accordance with the embodiment of FIG. 6 to be next described.

Figure 6:
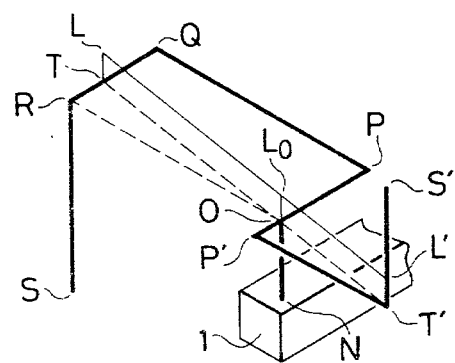
FIG. 6 is also a perspective view of the dynamical arrangement of a further example of the counterbalance device according to the invention.

FIG. 6 illustrates the dynamical arrangement of a still further example of the counterbalance device according to the invention. This version includes an arm section OP'T' which is fixedly connected to one end O of a manipulator arm OP and is bent by 90° so as to be parallel to the arm OP and an arm T'S' which is linked rotatably around a connection T' in a plane parallel to a plane SRO. The length and weight of the arm T'S' is determined so that it is in moment balance with the entire manipulator with the point O as the fulcrum. The arm P'T' is in parallel with the arm PQ and the position of the arm P'T' is such that the line along which the center of gravity of the counterbalance is moved by the rotation of the arm T'S' coincides with the gravity center movement line MM' described with reference to FIG. 3. The device further includes a rod LL' which has an arm TL which is fixedly connected to the arm QR at a position on the rotary arm QR or on the extension thereof. The rod LL' further includes a rotatable link L and a rotatable link L' on the arm T'S'. The links L and L' are coupled to each other through a slidable support point Lo on the extension of the arm NO so that a parallelogram TLL'T' is maintained. Thus, rotation of the arm RS of the manipulator is transmitted through the rod LL' to the arm T'S' of the counterbalance and, accordingly, moment unbalance due to the movement of the center of gravity of the manipulator is entirely eliminated which fully satisfies the moment balancing condition described with reference to FIG. 3.

In the examples shown in FIGS. 4, 5 and 6, it is unnecessary to provide the slidable support point Lo if the rod LL' is strong enough to maintain itself straight. In order to increase the strength of the coupling rod LL', additional coupling rods similar to the rod LL' may be provided above and below the fulcrum O in cooperation with one another. In this case also, the same effect is obtained. Furthermore, the coupling rod may be constituted by an upper rod and a lower rod which are connected with a rotatable auxiliary rod which is in parallel with the arm RS thereby also producing the same effect.

As is clear from the above-described examples, in the laser knife device according to the invention, movement of the center of gravity of the manipulator caused by movement of the manipulator arm effected by the operator is precisely counterbalanced so that moment unbalance attributed to movement of the center of gravity of the manipulator is eliminated resulting in very smooth mechanical motion at all times. Accordingly, the operator can freely and smoothly apply the laser beam to a desired position in the field of operation. Thus, the invention is believed to represent a significant contribution to the field of clinical operations.

What is claimed is:

1. A counterbalance device for a laser knife having a manipulator and comprising: means for counterbalancing said manipulator, said counterbalance means being coupled to said manipulator at a fulcrum, said counterbalance means so arranged that at an initial position thereof, moment balance with respect to said manipulator and said counterbalance means is maintained at said fulcrum and the centers of gravity of said manipulator and counterbalance means being in the same vertical plane wherein said manipulator and said counterbalancing means each comprise a plurality of arms, said arms being joined to one another only with rotary joints, and during operation of said device a plane along which the center of gravity of said manipulator moves is parallel to a plane along which the center of gravity of said counterbalance means moves in such a manner as to eliminate moment unbalance attributed to movement of the center of gravity of said manipulator at all positions within its range of movement.

2. A device as claimed in claim 1 wherein said counterbalance means comprises: a counterbalance arm section geometrically similar to a corresponding manipulator arm section and fixedly connected to one end of an arm of said manipulator arm section, the weight of said counterbalance arm section being determined so as to be in moment balance with said manipulator arm section with said one end of said arm of said manipulator section acting as said fulcrum, a rotatable manipulator arm linked to a coupling point so as to be rotatable around an end arm of said counterbalance arm section, the length and weight of said rotatable arm being determined so as to be in moment balance with a corresponding rotatable arm of said manipulator with respect to said fulcrum, and a rod and rotatable links for coupling ends of said rod respectively to said rotatable arms of said manipulators and counterbalance means so as to form a quadrilateral parallelogram at all positions of said manipulator with the corners of said parallelogram being formed by the ends of said rod and the junctures of said rotatable arms with said end arms so as to eliminate moment unbalance attributed to movement of the center of gravity of said manipulator.

3. A device as claimed in claim 1 wherein said device comprises: an arm fixedly connected to one end of an arm of said manipulator arm section at said fulcrum, the length and weight of said arm being selected so as to be in moment balance with said manipulator arm section at said fulcrum, a first arm of said counterbalance means fixedly coupled to said one end of said arm of said manipulator arm section and extending parallel to a corresponding arm of said manipulator arm section, a second arm of said counterbalance means linked so as to be rotatable around a connection point in a plane in which lies said first arm and a rotatable arm of said manipulator, the length and weight of said second arm being selected so as to be in moment balance with said rotatable arm of said manipulator with respect to said fulcrum, and a rod and rotatable links for rotatably coupling ends of said rod respectively to said rotatable arms of said manipulator and counterbalance means.

4. A device as claimed in claim 1 wherein said device comprises: a counterbalance arm section fixedly connected to one end of a first manipulator arm at said fulcrum and having a 90° bend at a connection point on a first arm of said counterbalance arm section forming an extension of said manipulator arm at which is joined a first end of a second arm of said counterbalance arm section which is parallel to a second arm of said manipulator joined to said first manipulator arm, a rotatable arm linked so as to be rotatable around a second end of said second arm of said counterbalance arm section in parallel with a plane formed by a rotatable arm of said manipulator joined to an end of a third arm of said manipulator the other end of which is joined to said second arm of said manipulator and a line between said fulcrum and the juncture between said rotatable arm of said manipulator and said third arm, the length and weight of said rotatable arm being so selected as to maintain moment balance with said manipulator with respect to said fulcrum, an arm fixedly connected to said third arm of said manipulator, and a rod and rotatable links coupling ends of said rod respectively to said arm fixedly connected to said third arm of said manipulator and said rotatable arm of said counterbalance means wherein a quadrilateral parallelogram is formed by the ends of said rod, the juncture point of said third arm of said manipulator and said arm connected thereto, and said fulcrum, said parallelogram being maintained for all positions of said manipulator.

5. A device as claimed in claim 1 wherein said plane along which the center of gravity of said manipulator moves is spaced apart from said plane along which the center of gravity of said counterbalance means moves.

* * * * *